United States Patent [19]

Danby

[11] E Patent Number: Re. 33,021

[45] Reissued Date of Patent: Aug. 15, 1989

[54] DUAL SOURCE PARENTERAL INFUSION APPARATUS

[75] Inventor: Hal C. Danby, Chilton, United Kingdom

[73] Assignee: Critikon, Inc., Tampa, Fla.

[21] Appl. No.: 165,682

[22] Filed: Mar. 8, 1988

Related U.S. Patent Documents

Reissue of:

[64] Patent No.: 4,576,592
Issued: Mar. 18, 1986
Appl. No.: 480,527
Filed: Mar. 30, 1983

[51] Int. Cl.[4] ..... A61M 5/16

[52] U.S. Cl. ..... 604/80; 604/253

[58] Field of Search ..... 604/80, 81, 253, 246, 604/65–67; 137/487.5, 486, 100, 101.19; 128/DIG. 12, DIG. 13

[56] References Cited

U.S. PATENT DOCUMENTS

| | | | |
|---|---|---|---|
| 3,601,124 | 8/1971 | Petree . | |
| 3,886,397 | 6/1975 | Bobo et al. . | |
| 3,982,534 | 9/1976 | Buckman | 604/81 |
| 4,034,759 | 8/1975 | Virag . | |
| 4,038,981 | 8/1977 | Le Fevre et al. . | |
| 4,094,318 | 6/1978 | Burke et al. | 604/81 X |
| 4,105,028 | 8/1978 | Sadlier et al. . | |
| 4,105,029 | 8/1978 | Virag . | |
| 4,114,617 | 9/1978 | Turner et al. . | |
| 4,219,022 | 8/1980 | Genese . | |
| 4,223,695 | 9/1980 | Muetterties | 137/173 |
| 4,236,515 | 12/1980 | Genese . | |
| 4,237,880 | 12/1980 | Genese . | |
| 4,238,879 | 12/1980 | Genese . | |
| 4,250,879 | 2/1981 | Muetterties . | |
| 4,252,116 | 2/1981 | Genese et al. . | |
| 4,256,103 | 3/1981 | Mylrea . | |
| 4,256,105 | 3/1981 | Leahey et al. . | |
| 4,256,240 | 5/1981 | Jenkins . | |
| 4,258,712 | 3/1981 | Harms et al. . | |
| 4,261,388 | 4/1981 | Shelton . | |
| 4,300,552 | 11/1981 | Cannon . | |
| 4,324,238 | 4/1982 | Genese et al. . | |
| 4,391,598 | 7/1983 | Thompson | 604/65 |
| 4,430,074 | 2/1984 | Mooring | 604/49 |
| 4,447,230 | 5/1984 | Gula et al. | 604/122 |
| 4,451,255 | 5/1984 | Bujan et al. | 604/157 |

FOREIGN PATENT DOCUMENTS

| | | |
|---|---|---|
| 2059776 | 4/1981 | United Kingdom . |

*Primary Examiner*—Stephen C. Pellegrino
*Attorney, Agent, or Firm*—W. Brinton Yorks, Jr.

[57] ABSTRACT

A dual parenteral solution apparatus for delivering predetermined volumes of two solutions at predetermined flow rates with increased accuracy. The apparatus has a shut-off valve in the supplementary solution supply system which is immediately activated when the supplemental solution supply is depleted.

18 Claims, 2 Drawing Sheets

DUAL SOURCE PARENTERAL INFUSION APPARATUS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to an apparatus for administering parenteral solutions to medical patients. In particular, this application is directed to an improved apparatus for delivering precise volumes of solutions at precise rates from more than one solution source.

2. Description of the Prior Art

Infusion delivery systems for delivering liquid to a patient from more than one solution source have been previously known. The most common systems use gravity flow and manually adjustable tubing clamps or pinch valves. They may employ a variety fo valves and junctions to control flow at the desired rate and sequence. Examples of such systems are described in U.S. Pat. Nos. 3,886,937; 4,034,754; 4,114,617; 4,219,022; 4,223,695; 4,236,515; 4,237,879; 4,237,880; 4,250,879; 4,252,116; 4,256,104; 4,256,105; and 4,258,712. Dual delivery systems relying on electronic flow control means are described in U.S. Pat. No. 4,094,318, for example.

Automatic flow control systems relying on a drop counter which measures the frequency of drop fall through a drip chamber have been previously known. In general, a light beam from a lamp to a light detector is positioned so that it is interrupted by drops falling through a drip chamber. The frequency of the breaking of the light beam and/or the time lapse between drops breaking the light beam are directly proportional to the flow rate and are used to determine adjustments to be made to a flow control valve to change flow to the desired rate. Examples of systems comprising drop counters and control systems responsive thereto are described in U.S. Pat. Nos. 3,163,179; 3,601,124; 3,886,937; 4,038,982; 4,314,567.

The prior art systems do not provide the precise control of the total delivered volume of small quantities of secondary solutions which can be obtained with the apparatus of this invention.

SUMMARY AND OBJECTS OF THE INVENTION

It is an object of this invention to provide a system which can provide precise volumes of primary and secondary solutions to a patient at precise flow rates.

The parenteral infusion apparatus of this invention for delivering parenteral solutions from two sources comprises a first drip chamber with a primary flow sensor means associated therewith for detecting liquid flow rate through the primary drip chamber and a supplemental solution drip chamber with supplemental solution flow sensor means associated therewith for detecting liquid flow rate through the supplemental solution drip chamber. The outlet of the supplemental solution drip chamber is connected with the primary drip chamber inlet by conduit means having a shut-off control system means associated therewith. The shut-off control system includes means for terminating supplemental solution flow through the conduit when the measured flow detected in the supplemental solution drip chamber is less than the flow detected in the primary drip chamber.

The apparatus of this invention is particularly useful when the supplemental solution or secondary drip chamber and the supplemental solution or secondary solution source associated therewith is remote from the controller.

DETAILED DESCRIPTION OF THE INVENTION

Figure 1:
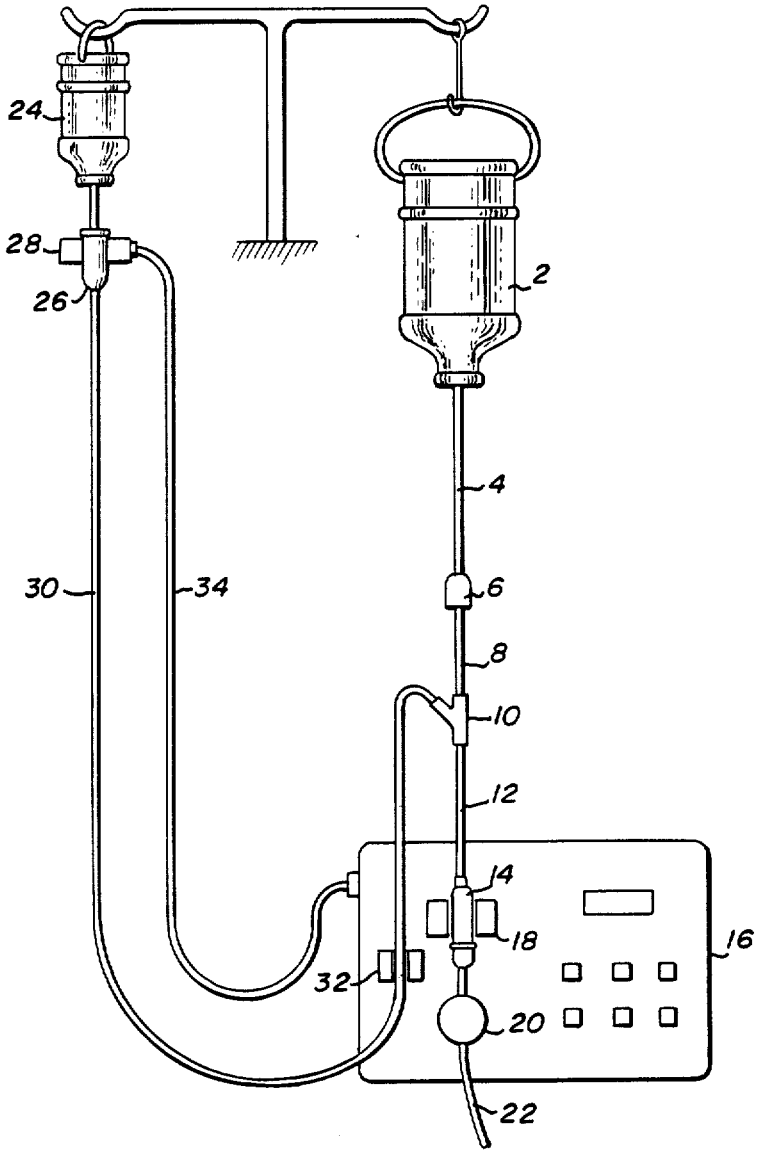
FIG. 1 is a schematic representation of the dual source parenteral infusion apparatus of this invention.

The parenteral administration of medical liquids to patients is a routine, long established practice. Aqueous solutions of amino acids, dextrose, electrolytes and saline are commonly administered to patients over prolonged periods of time. Frequently, the patient must be administered a supplemental solution. Preferably, this supplemental solution is administered through the same hypodermic needle to avoid unnecessary pain and the trauma to the patient of additional punctures. To avoid dilution and incompatibility problems, it is also preferred that the flow of the primary solution be temporarily interrupted during administration of the secondary solution. After administration of the secondary fluid is completed, flow of the primary liquid is resumed.

Both fluids are usually supplied to the patient by gravity flow. The secondary fluid source is maintained at a higher elevation than the primary solution source, and the secondary fluid supply is therefore relatively more remote from the primary liquid source and controller. As a consequence, the connective tubing leading from the supplemental fluid source systems is frequently much longer and has a greater internal volume than other tubing in the system.

The supplemental supply system is primed by squeezing sidewalls of the supplemental drip chamber together with the supplemental drip chamber outlet conduit being pinched closed. Air is expelled from the drip chamber into the supplemental solution container. As the drip chamber sidewalls return to their original shape, liquid is drawn from the supplemental solution container into the drip chamber, preferably to a level at about the middle of the drip chamber. The supplemental drip chamber outlet conduit is then opened, permitting supplemental solution to enter the drip chamber and an equal volume to pass through the drip chamber outlet conduit. When the air has been displaced from the outlet conduit, it is connected to the primary solution supply conduit, typically through a "Y" connection or junction. The supplemental solution supply conduit is usually primed with a standard, large volume parenteral solution.

Routine administration of small, precise volumes of solutions such as antibiotics, tranquilizers, cardiovascular drugs and the like as supplemental solutions to an established primary parenteral solution administration apparatus has not been practical prior to this invention. A substantial proportion of supplemental solution may be required to fill the tubing, particularly if a small volume of supplemental solution is to be administered. Usually the supplemental solution is reconstituted by adding water to the vial containing moisture-free drug. The dried contents are precise, but the volume of water added may be approximate. To accurately administer drug to the patient, therefore, is is necessary to completely empty the supplemental solution container or vial. This frequently draws air into the supplemental solution drip chamber and into the outlet conduit leading therefrom. Air trapped in the outlet conduit can be removed only by disconnecting the supplemental system and repriming it. This problem is solved by the apparatus of this invention.

Referring to FIG. 1, a schematic representation of the dual source parenteral infusion delivery apparatus is illustrated. The primary solution container 2 is connected through connective tubing 4 to the check valve 6. Connective tubing 8 leads from the check valve 6 to the "Y"-junction 10. The outlet of the junction 10 is connected with the primary drip chamber 14 by connective tubing 12. The controller 16 has a drop sensor 18 and precision flow control valve 20. The drop sensor 18 counts the drops and measures the drop rate. This correlates directly to the flow rate, and the valve 20 is adjusted to correct for any variance from the desired flow rate. Connective tubing 22 leads from the control valve 20 to the patient.

The supplementary solution container 24 is supported at a higher elevation than the primary solution container 2, and a supplementary solution drip chamber 26 is provided immediately below the secondary solution container to minimize the internal volume of connecting tubing or other connecting elements. Secondary drop sensor 28 is a means for counting drops falling through the secondary drip chamber 26. Connecting tubing 30 leading from the drip chamber 26 passes through an on-off pinch valve 32 of the controller 16 and then to the supplementary solution inlet of the junction 10. Connecting cable 34 leads to the controller 16 from the supplementary drop sensor 28. Cable 34 is used to provide light or electric lighting power to the supplemental solution drop sensor 28. It also transmits light or electrical signals produced in response to falling drops or drop counts corresponding thereto from the supplementary solution drop sensor 28 as will be described in conjunction with a description of the drop sensors shown in FIG. 2–4.

While flow of supplementary solution continues through drip chamber 26, tubing 30, junction 10, tubing 12 and drip chamber 14, drop counts in drip chambers 26 and 14 are the same. However, when the supplementary solution is depleted, drop fall in the drip chamber 26 will decline and stop while flow of residual solution in drip chamber 26 and tubing 34 will continue. In the apparatus of this invention, if the drop count supplementary solution as measured in drip chamber 26 falls below the drop count measured in drip chamber 14, the pinch valve 32 immediately closes, terminating further solution flow from the drip chamber 26 through conduit 30. The back pressure on the check valve 6 is then reduced, and the check valve opens, reinitiating primary solution flow through the "Y"-junction 10. Subsequent administration of the supplementary solution will begin and end with almost identical levels of supplementary solution in drip chamber 26 since significant air flow into drip chamber 26 is prevented. This permits very precise solution administration. With prior art systems, air intrusion into conduit 30 would have occurred, requiring repriming and inaccurate administration since an unpredictable and underdetermined amount of supplementary solution would remain in the connecting tubing.

Figure 2:
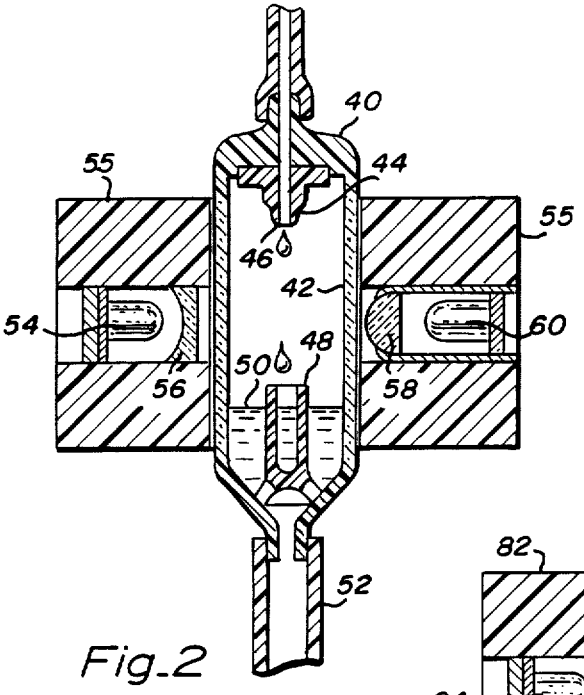
FIG. 2 is a cross-sectional view of a drip chamber and drop sensor combination of this invention.

Referring to FIG. 2, a cross-sectional representation of a drip chamber and a drop sensor assembly comprising a lamp light source and a light sensor combination are shown. The drip chamber 40 is of standard construction having transparent and flexible plastic sidewalls 42. The size of the orifice 46 in the drop former 44 determines the size of the droplets formed. The falling drops impinge on the anti-splash element 48, reducing air-liquid mixing. A constant liquid level 50 is maintained in the drip chamber 40 to prevent passage of air from the drip chamber 40 to the outlet conduit 52.

Light from the lamp 54 mounted in housing 55 passes through a concave lens 56 and as a parallel beam passes through the walls 42, impinging on the convex lens 58 which focus the transmitted light on the light sensor 60, creating a voltage between light sensor electrical leads (not shown). Interruption of the light beam passing between the lamp 54 and light detector 60 by passage of falling drops therethrough causes an abrupt change in the electrical voltage which can be easily detected and counted by conventional systems known in the art. Each interruption corresponds to the passage of a drop. Both the primary drop detector 18 and supplemental drop detector 28 in the apparatus of FIG. 1 can be constructed as shown in FIG. 2.

Because the supplementary solution drop detector is remote from the controller, electrical wire leads from the light sensor to the controller can be a source of extraneous electrical signals (noise). It is therefore desired to construct the drop detector and output signal transmission system therefore in such a manner that signal interference from extraneous sources is eliminated during transmission to the controller or its effects minimized.

In one embodiment, the light signal generated by the light detector 60 is amplified by conventional means prior to transmission to the controller so that the comparative magnitude of the desired signal is far greater than the interfering signals and the noise effect is not significant.

Figure 3:
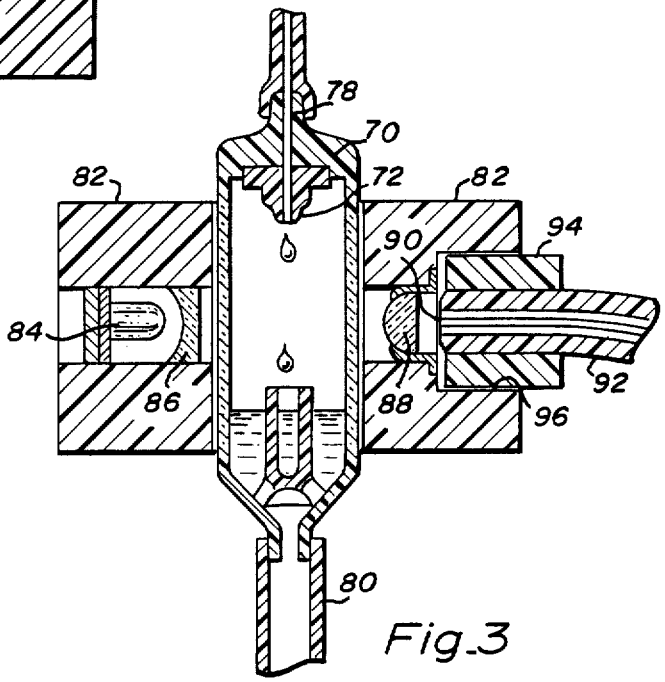
FIG. 3 is a cross-sectional view of an alternate embodiment of a supplemental solution drip chamber and drop sensor combination with a fiber optics light sensor.
Figure 4:
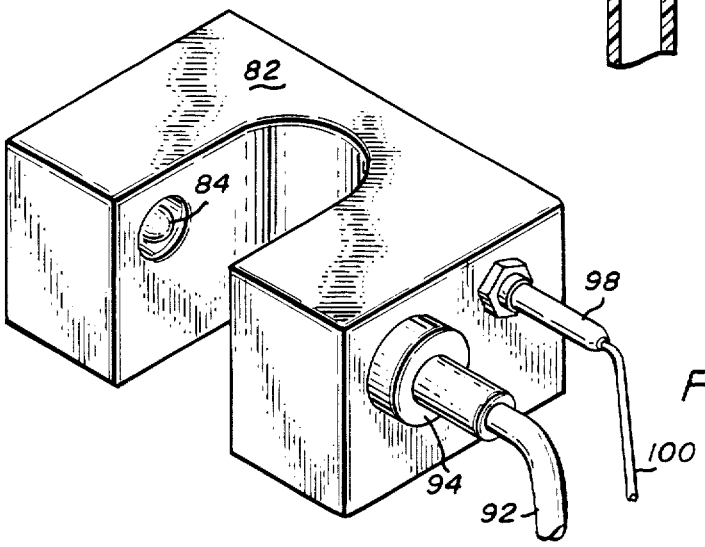
FIG. 4 is an isometric view of the drop sensor embodiment with a fiber optics light sensor.

FIGS. 3 and 4 are directed to an alternative embodiment of the supplementary solution drop detector employing fiber optics. In this system, transmitted light is conducted to a light sensor in the controller by means of the fiber optics cable, and extraneous electrical interference arising during transmission is eliminated. The drop chamber 70, drop former 72 and anti-splash element 74, are the same as described above with respect to FIG. 2. The liquid level 76 is maintained by terminating fluid flow when the differential drop rates are detected. Supplementary solution is introduced through conduit 78 and is removed through outlet tubing 80. In this embodiment, however, the light originating from the lamp 84 in the housing 82, after passing through the concave lens 86 and drip chamber walls 87, is focused by convex lens 88 on the end 90 of the fiber optics cable 92. The fiber optics cable 92 has a terminal male connector 94 which connects with the corresponding receptor socket recess 96 in housing 82. Light emitted at the other end of the fiber optics cable is sensed by a light sensor in the controller in a conventional manner. The light deflection occasioned by the passage of a drop through the supplemental solution drip chamber effects an electrical signal deflection from the light detector in the same manner as described above with regard to the embodiment in FIG. 2.

FIG. 4 is an isometric view of the light sensor housing 82 showing the relative locations of the lamp 84, the jack connector 98 of the electric cable 100 for the lamp 84, the fiber optics cable 92 and connector 94.

The invention claimed is:

1. A parenteral infusion apparatus for delivering parenteral solutions from two sources comprising a first drip chamber with a primary flow sensor means associated therewith for detecting liquid flow rate through the primary drip chamber, a supplemental solution drip chamber with supplemental solution flow sensor means associated therewith for detecting liquid flow rate through the supplemental solution drip chamber, the outlet of the supplemental solution drip chamber being connected with the primary drip chamber inlet by conduit means having a shut-off control system means associated therewith for terminating supplemental solution flow through the conduit when the measured flow detected in the supplemental solution drip chamber is less than the flow detected in the primary drip chamber.

2. The parenteral infusion apparatus of claim 1 wherein the supplemental solution drip chamber is remote from the primary drip chamber.

3. The parenteral infusion apparatus of claim 1 wherein the flow sensor means is a means for detecting passage of individual drops falling through the supplemental solution drip chamber.

4. The parenteral infusion apparatus of claim 3 wherein the supplemental solution flow sensor means comprises a light source for directing light through the path of drops falling in the supplemental solution drip chamber and a light collector means for focusing light transmitted through the supplemental solution drip chamber.

5. The parenteral infusion apparatus of claim 4 wherein the light is focused on a light sensor.

6. The parenteral infusion apparatus of claim 5 wherein the electrical signal from the light sensor is amplified and transmitted to a controller.

7. The parenteral infusion apparatus of claim 4 wherein the light is focused on the end of a fiber optics cable in optical communication with a light sensor means in a controller.

8. The parenteral infusion apparatus of claim 4 wherein the light source is a light-emitting diode.

*9. A parenteral infusion apparatus for delivering parenteral solutions from two sources comprising:*

*a primary solution source;*

*a first conduit means for conducting solution supplied by said primary solution source;*

*a check valve located in said first conduit means;*

*a supplementary solution source;*

*a second conduit means for conducting solution supplied by said supplementary solution source;*

*an outlet conduit leading to a patient site;*

*a junction means for connecting said first conduit means and said second conduit means to said outlet conduit;*

*wherein the flow path of said primary solution includes said first conduit means, said check valve, said junction means, and said outlet conduit, and the flow path of said supplementary solution includes said second conduit means, said junction means, and said outlet conduit;*

*controller means, engaging said second conduit means, and including means for selectively occluding said second conduit means to terminate solution flow from said supplementary solution source, and further including a flow control valve means engaging said outlet conduit for controlling the flow therethrough; and*

*primary flow sensor means located in said primary solution flow path for detecting the liquid flow rate of solution therethrough, and supplementary flow sensor means located in said supplementary solution flow path between said supplementary solution source and said engagement of said second conduit means with said controller means for detecting the liquid flow rate of solution therethrough,*

*wherein said controller means is responsive to said flow sensor means for controlling said selectively occluding means and said flow control valve means.*

*10. The parenteral infusion apparatus of claim 9, wherein said controller means for selectively occluding said second conduit means comprises a pinch valve engaging said second conduit means.*

*11. The parenteral infusion apparatus of claim 10, wherein said junction means comprises a "Y" connection.*

*12. The parenteral infusion apparatus of claim 11, wherein said check valve is closed when said supplementary solution is flowing through said second conduit means, and said check valve opens in response to a reduction in back pressure when said second conduit means is occluded.*

*13. The parenteral infusion apparatus of claim 12, wherein said primary flow sensor means includes a drop sensor opposing a drip chamber.*

*14. The parenteral infusion apparatus of claim 13, wherein said supplementary flow sensor means is connected to said second conduit means.*

*15. The parenteral infusion apparatus of claim 14, wherein said supplementary flow sensor means includes a second drop sensor opposing a second drip chamber connected to said outlet conduit.*

*16. A parenteral infusion apparatus for delivering parenteral solutions from two sources comprising:*

*first tubing for delivering a primary solution;*

*second tubing for delivering a supplementary solution;*

*connective tubing leading to a patient site;*

*means for connecting said first tubing and said second tubing to said connective tubing;*

*wherein the flow path of said primary solution includes said first tubing, said connecting means, and said connective tubing, and the flow path of said supplementary solution includes said second tubing, said connecting means, and said connective tubing;*

*means, located in said flow path of said primary solution, for alternately allowing primary solution or supplementary solution to flow through said connective tubing; and*

*a controller, including means, located in said primary solution flow path, for sensing the flow of solution therethrough, and means, connected to said second tubing, for sensing the flow of said supplementary solution, and having a pinch valve for selectively occluding said second tubing and a flow control valve for adjusting the flow rate through said connective tubing.*

*17. A parenteral infusion apparatus for delivering parenteral solutions from two sources comprising:*

*first conduit means for delivering a primary solution;*

*second conduit means for delivering a supplementary solution;*

*connective tubing leading to a patient site;*

*means for connecting said first conduit means and said second conduit means to said connective tubing;*

*a controller, including first sensor means for detecting liquid flow through said second conduit means, second sensor means for detecting liquid flow through said connective tubing, means, responsive to said first sensor, for selectively occluding said second conduit means, and means, responsive to said second sensor means, for adjusting the flow rate through said connective tubing; and*

*means, in fluid connection with said first conduit means, for alternately allowing primary solution or supplementary solution to flow through said connective tubing.*

*18. A parenteral infusion apparatus for delivering parenteral solutions from two sources comprising:*

*a first conduit for delivering a primary solution;*

*a second conduit for delivering a supplementary solution and having a first flow sensor associated therewith;*

*a third conduit having a second flow sensor associated therewith;*

*a controller including a first valve engaging said second conduit and a flow control valve;*

*means for connecting said first, second and third conduits to said flow control valve; and*

*means, in fluid connection with said first conduit, for alternately allowing primary solution or supplementary solution to flow to said flow control valve,*

*wherein said controller is responsive to said first flow sensor for selectively occluding said second conduit and is responsive to said second flow sensor for adjusting said flow control valve.*

* * * * *